United States Patent

Hayakawa et al.

Patent Number: 5,463,053
Date of Patent: Oct. 31, 1995

[54] OPTICALLY ACTIVE PYRIDOBENZOXAZINE DERIVATIVES

[75] Inventors: Isao Hayakawa; Shohgo Atarashi; Yoichi Kimura; Katsuhiro Kawakami, all of Tokyo, Japan

[73] Assignee: Daiichi Pharmaceutical Co., Ltd., Tokyo, Japan

[21] Appl. No.: 183,783

[22] Filed: Jan. 21, 1994

Related U.S. Application Data

[63] Continuation of Ser. No. 798,151, Nov. 26, 1991, abandoned.

[30] Foreign Application Priority Data

Nov. 28, 1990 [JP] Japan ................... 2-327594

[51] Int. Cl.⁶ .................. C07D 215/56; A61K 31/47
[52] U.S. Cl. ........................................................ 544/101
[58] Field of Search ................ 544/101; 514/235.5

[56] References Cited

U.S. PATENT DOCUMENTS 4,753,953  6/1988  Masuzawa et al. .............. 544/101

FOREIGN PATENT DOCUMENTS 0208210  6/1986  Germany.
0206283  6/1986  Germany.
0393400  3/1990  Germany.

OTHER PUBLICATIONS

"Synthesis and Antibacterial Activities of Substituted 7-Oxo-2,3-dihydro-7H-pyrido[1,2,3-de] [1,4] benzoxazine-6-carboxylic Acids" by Isao Hayakawa, Tokiyuki Hiramitsu and Yoshiaki Tanaka; *Che. Pharm. Bull.* (1984) pp. 4907-4913.

*Primary Examiner*—Nicholas Rizzo
*Attorney, Agent, or Firm*—Sughrue, Mion, Zinn, Macpeak & Seas

[57] ABSTRACT

An optically active pyridobenzoxazine derivative represented by formula (I):

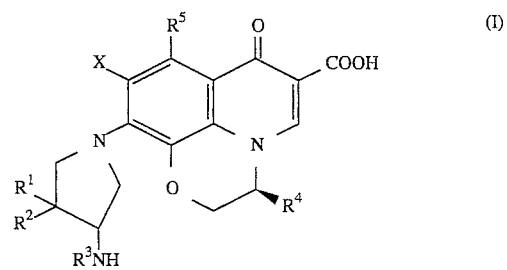

wherein $R^1$ and $R^2$ wherein $R^1$ and $R^2$, which may be the same or different, each represent an alkyl group having from 1 to 6 carbon atoms, a halogenated alkyl group having from 1 to 6 carbon atoms, a hydroxyalkyl group having from 1 to 6 carbon atoms, or an alkoxymethyl group having from 2 to 7 carbon atoms; $R^3$ represents a hydrogen atom, an alkyl group having from 1 to 6 carbon atoms, an acyl group having from 2 to 7 carbon atoms, a halogen-substituted or unsubstituted alkyloxycarbonyl group having from 2 to 7 carbon atoms, a phenylmethyloxycarbonyl group, or a phenylmethyloxycarbonyl group whose phenyl moiety is substituted with a halogen atom, a nitro group, or a methoxy group; $R^4$ represents a methyl or fluoromethyl group which is in a β-configuration; $R^5$ represents a hydrogen atom, an amino group, a hydroxyl group, a methyl group, or a halogen atom; and X represents a fluorine atom or a chlorine atom, and a salt thereof are disclosed. These compounds exhibit potent antimicrobial activity with broad antimicrobial spectra and improved lipophilic properties.

1 Claim, No Drawings

OPTICALLY ACTIVE PYRIDOBENZOXAZINE DERIVATIVES

This is a continuation of application Ser. No. 07/798,151, filed Nov. 26, 1991, now abandoned.

FIELD OF THE INVENTION

This invention relates to an antimicrobial compound useful as human and veterinary drugs, and fisheries drugs.

BACKGROUND OF THE INVENTION

Concerning pyridonecarboxylic acid type synthetic antimicrobial agents, it is known that the substituent at the 7-position of the quinoline skeleton thereof (or 10-position of the pyridobenzoxazine skeleton) has influences on antimicrobial activity. Various groups have been proposed as a substituent at the 7-position. In particular, pyridonecarboxylic acid derivatives having a 3-aminopyrrolidinyl group at the 7-position are known to exhibit potent antimicrobial activity and a broad antimicrobial spectrum against both Gram-negative and Gram-positive bacteria.

Pyridonecarboxylic acid derivatives comprised of a 3-aminopyrrolidinyl group and a pyridobenzoxazine skeleton are believed to have low lipophilic properties, and their pharmacokinetic properties are not good probably due to poor absorption from intestinal tracts.

SUMMARY OF THE INVENTION

An object of the present invention is to provide a 3-aminopyrrolidinyl-substituted pyridobenzoxazine derivative having improved lipophilic properties while exhibiting excellent antimicrobial activity against a broad range of microorganisms including Gram-positive bacteria.

The inventors have conducted extensive investigations and, as a result, found that the above object of the present invention is accomplished by an optically active pyridobenzoxazine derivative having a 3-aminopyrrolidinyl substituent in which the carbon atom adjacent to the carbon atom to which the amino group bonded is di-substituted with an alkyl group, i.e., an optically active 4-amino-3,3-dialkyl-substituted pyrrolidinyl group represented by a structural formula:

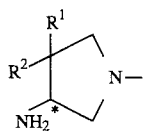

wherein $R^1$ and $R^2$, which may be the same or different, each represents an alkyl group having from 1 to 6 carbon atoms, a halogenated alkyl group having from 1 to 6 carbon atoms, a hydroxyalkyl group having from 1 to 6 carbon atoms, or an alkoxymethyl group having from 2 to 7 carbon atoms.

The compound according to the present invention includes, as a matter of course, the respective diastereomers which are present as stereo isomers attributed to its asymmetric carbon atoms.

The present invention provides an optically active pyridobenzoxazine derivative represented by formula (I):

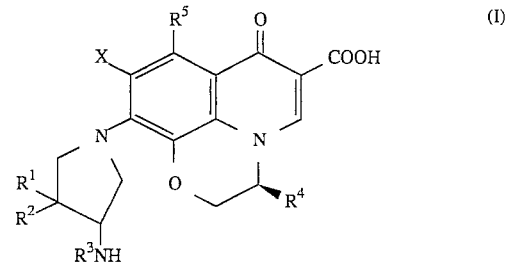

wherein $R^1$ and $R^2$ are as defined above; $R^3$ represents a hydrogen atom, an alkyl group having from 1 to 6 carbon atoms, an acyl group having from 2 to 7 carbon atoms, a halogen-substituted or unsubstituted alkyloxycarbonyl group having from 2 to 7 carbon atoms, a phenylmethyloxycarbonyl group, or a phenylmethyloxycarbonyl group whose phenyl moiety may substituted with a halogen atom, a nitro group, or a methoxy group; $R^4$ represents a methyl or fluoromethyl group which is in a β-configuration; $R^5$ represents a hydrogen atom, an amino group, a hydroxyl group, a methyl group, or a halogen atom; and X represents a fluorine atom or a chlorine atom, and a salt thereof.

DETAILED DESCRIPTION OF THE INVENTION

In formula (I), $R^1$ and $R^2$, which may be the same or different, each preferably represent an alkyl group having from 1 to 6 carbon atoms, e.g., a methyl group, an ethyl group, a propyl group, and a butyl group; a halogenated alkyl group having from 1 to 6 carbon atoms, e.g., a fluoromethyl group, a trifluoromethyl group, and a chloroethyl group; a hydroxyalkyl group having from 1 to 6 carbon atoms, e.g., a hydroxymethyl group, a hydroxyethyl group, and a hydroxypropyl group; and an alkoxymethyl group having from 2 to 7 carbon atoms, e.g., a methoxymethyl group, an ethoxymethyl group, and a propoxymethyl group. More preferred of them are an alkyl group, a hydroxyalkyl group, and a halogenated alkyl group. The most preferred are a methyl group, an ethyl group, a fluoromethyl group, and a hydroxymethyl group.

$R^3$ preferably represents a hydrogen atom, an alkyl group having from 1 to 6 carbon atoms, e.g., a methyl group, an ethyl group, a propyl group, and a butyl group; an acyl group, e.g., an acetyl group, a benzoyl group, and a chloroacetyl group, a t-butoxycarbonyloxy group, a 2,2,2-trichloroethoxycarbonyl group, a benzyloxycarbonyl group, and a phenylmethyloxycarbonyl group, e.g., a p-nitrobenzyloxycarbonyl group. More preferred of them are a hydrogen atom, a methyl group, an ethyl group, and a propyl group, with a hydrogen atom being the most preferred.

$R^4$ represents a methyl group or a fluoromethyl group, and preferably a methyl group. The carbon atom at which $R^4$ is bonded is an asymmetric carbon atom. It is considered that more potent antimicrobial activity would be exerted with this asymmetric carbon atom in a p-configuration. In this case, the absolute configuration is an (S)-configuration where $R^4$ is a methyl group, and an (R)-configuration where $R^4$ is a fluoromethyl group.

$R^5$ represents a hydrogen atom, an amino group, a hydroxyl group, a methyl group, or a halogen atom, and preferably a hydrogen atom.

X represents a fluorine atom or a chlorine atom, and preferably a fluorine atom.

The compounds of the present invention are characterized by having a 4-amino-3,3-dialkyl-substituted pyrrolidinyl group at the 10-position of the pyridobenzoxazine skeleton. Specific examples of the 4-amino-3,3-dialkylpyrrolidinyl group include a 4-amino-3,3-dimethylpyrrolidinyl group, a 4-amino-3-ethyl-3-methylpyrrolidinyl group, a 4-amino-3,3-bis(fluoromethyl)pyrrolidinyl group, and a 4-amino-3,3-bis(hydroxymethyl)pyrrolidinyl group, each of which is optically active, with a 4-amino-3,3-dimethylpyrrolidinyl group being particularly preferred.

These 4-amino-3,3-dialkylpyrrolidinyl groups produce stereoisomers ascribed to the asymmetric carbon atom to which the amino group is bonded. The steric configuration at the carbon atom to which the amino group is bonded is preferably an (S)-configuration from the standpoint of antimicrobial activity exerted. In the pyridonebenzoxazine skeleton, on the other hand, the carbon atom to which $R^4$ is bonded is an asymmetric carbon atom. The substituent $R^4$ at this asymmetric carbon atom is in a β-configuration for obtaining higher antimicrobial activity.

Thus, the compounds of the present invention each contain at least two asymmetric carbon atoms. That is, there are at least four stereoisomers for each compound, including diastereomers. For use as a synthetic antimicrobial agent, a compound solely comprising one stereoisomer is preferred in many cases to a mixture of these stereoisomeric isomers.

The compounds of the present invention can be synthesized by reacting 9,10-difluoro-2,3-dihydro-3-(S)-3-methyl-7-oxo-7H-pyrido[1,2,3-de][1,4]benzoxazine-6-carboxylic acid or a difluoroborate thereof (i.e., a compound having a -C(=O)O-BF$_2$ moiety instead of COOH at 6 position) with a 4-amino-3,3-dialkylpyrrolidine in a solvent in the presence of a base.

The difluoroborate is easily prepared from a corresponding free carboxylic acid with an appropriate boron trifluoride compound, e.g., boron trifluoride ether complex, as disclosed in U.S. Pat. No. 5,053,407.

The reaction for introducing a 4-amino-3,3-dialkylpyrrolidine is usually carried out in the presence of an acid scavenger. The acid scavenger to be used includes organic bases and inorganic bases, and organic bases are generally used for preference.

The organic bases preferably include tertiary amines. Specific examples of suitable tertiary amines are trialkylamines, e.g., triethylamine, tripropylamine, N,N-diisopropylethylamine, and tributylamine; anilines, e.g., N,N-dimethylaniline and N,N-diethylaniline; and heterocyclic compounds, e.g., N-methylmorpholine, pyridine, and N,N-dimethylaminopyridine.

Usable inorganic bases include hydroxides, carbonates, or hydrogencarbonates of alkali metals such as lithium, sodium, and potassium, e.g., lithium hydroxide, sodium hydroxide, potassium hydroxide, anhydrous sodium carbonate, anhydrous potassium carbonate, sodium hydrogencarbonate, and potassium hydrogencarbonate.

The 4-amino-3,3-dialkylpyrrolidine as one of the reactants may be used in an amount at least twice the equivalent necessary for the reaction so as to serve also as an acid scavenger.

Solvents which can be used in the reaction are not particularly limited as long as they are inert to the reaction and include, for example, acetonitrile; amides, e.g., N,N-dimethylformamide, N-methyl-2-pyrrolidone, and N,N-dimethylacetamide; aromatic hydrocarbons, e.g., benzene, toluene, and xylene; aprotic polar solvents, e.g., dimethyl sulfoxide and sulfolane; lower alcohols, e.g., methanol, ethanol, propanol, butanol, amyl alcohol, isoamyl alcohol, cyclohexyl alcohol, and 3-methoxybutanol; and ethers, e.g., dioxane, dimethyl cellosolve, diethyl cellosolve, and diglyme. Water-soluble solvents may be used as an aqueous solvent. This being the case, it is recommended to use an organic base as an acid scavenger.

The reaction temperature ranges from room temperature to about 180° C. The reaction completes in about 10 minutes to about 48 hours and usually from about 30 minutes to about 30 hours.

Where a 4-amino-3,3-dialkylpyrrolidine to be introduced contains a protected group on its pyrrolidine ring, the protective group can be removed after the reaction in a usual manner selected according to the protective group.

The 4-amino-3,3-dialkylpyrrolidine, for example, 4-amino-3,3-dimethylpyrrolidine, can be synthesized according to Reference Examples hereinafter described and may also be obtained according to the reaction scheme shown below.

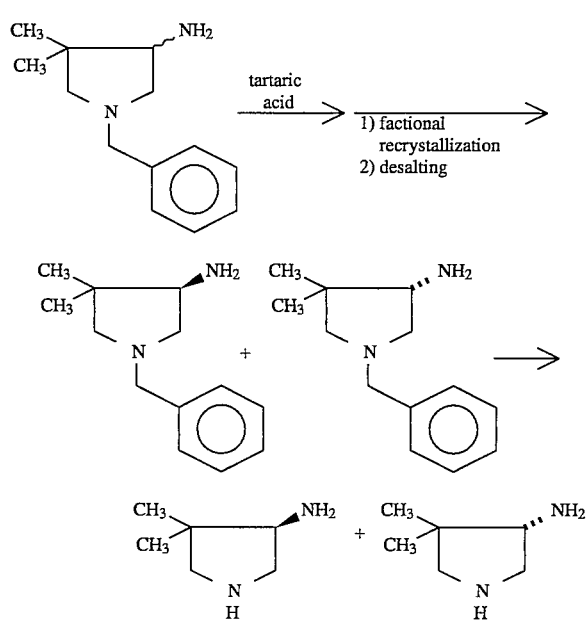

Where a difluoroborate compound in which the carboxyl group at the 6-position is borated is used as a starting compound, the resulting product can be converted to a free carboxylic acid by treating with an protic substance, such as water and alcohols. For example, the product is treated with ethanol in the presence of triethylamine either in the presence or absence of an acid scavenger.

The resulting pyridonecarboxylic acid derivative of formula (I) is purified by recrystallization, reprecipitation, treatment with activated carbon, chromatography, or the like means either individually or in combination thereof.

The pyridonecarboxylic acid derivatives having a 4-amino-3,3-dialkylpyrrolidinyl group according to the present invention have improved lipophilic properties over the corresponding compounds having an aminopyrrolidinyl group without the alkyl groups and are therefore expected to be sufficiently absorbed through oral administration to thereby manifest more excellent antimicrobial activity.

The pyridonecarboxylic acid derivatives according to the present invention can be used as free compounds, acid addition salts or salts of the carboxyl groups thereof. Examples of such acid addition salts include inorganic acid salts such as hydrochloride, sulfate, nitrate, hydrobromide, hydroiodide, and phosphate; and organic acid salts such as acetate, methanesulfonate, benzenesulfonate, toluenesulfonate, citrate, maleate, fumarate, and lactate.

Examples of the salts of carboxyl groups include inorganic and organic salts, for example, alkali metal salts such as lithium salts, sodium salts and potassium salts, alkaline earth metal salts such as magnesium salt and calcium salt, ammonium salts, triethylamine salt, N-methylglucamate and tris(hydroxymethyl)aminomethane salt.

These free compounds, acid addition salts, and salts of carboxyl groups of pyridobenzoxazine-6-carboxylic acid derivatives may exist as hydrates.

On the other hand, pyridobenzoxazine-6-carboxylic acid derivatives whose the carboxyl moieties are esters are useful as synthetic intermediates or prodrugs. For example, alkyl esters, benzyl esters, alkoxyalkyl esters, phenylalkyl esters, and phenyl esters are useful as synthetic intermediates.

The esters useful as prodrugs are those which are readily cleaved in the living body to give a free carboxylic acid. Thus, for example, the acetoxymethyl ester, pivaloyloxymethyl ester, ethoxycarbonyloxy ester, choline ester, dimethylaminoethyl ester, 5-indanyl ester, phthalidinyl ester, 5-substituted-2-oxo-1,3-dioxol-4-yl-methyl ester, and various oxoalkyl esters such as 3-acetoxy-2-oxobutyl ester are suitable.

The compounds of the present invention have potent antimicrobial activity and thus can be used as human and veterinary medicines, fish medicines, agricultural chemicals, or food preservatives.

The dose of the compound of the present invention as the active ingredient of medicine for human use is in the range of from 50 mg to 1 g, and preferably from 100 mg to 300 mg, per day for adult. The dose for medicine for use with animals is in the range of from 1 to 200 mg, and preferably from 5 to 100 mg, per kg of body weight per day. The daily dose should be adjusted in accordance with such factors as intended use (such as therapeutic or preventive), kind, size or age of the human or the animal to be cured, the kind of the pathogenic organisms, to be treated symptoms exhibited, etc.

The above-mentioned daily dose may be divided into 1 to 4 times per day. It may be necessary to deviate from the above-recited amount according to causative organisms or the severity of the symptoms exhibited.

The compounds according to the present invention are active against a very broad spectrum of microorganisms causing various infectious diseases and it is possible to prevent, alleviate and/or cure the diseases caused by such pathogens. Examples of susceptible bacteria or bacteria-like microorganisms on which the compounds of the present invention are effective include Staphylococcus sp., *Streptococcus pyogenes, Streptococcus haemolyticus, Streptococcus fecalis, Streptococcus pneumoniae*, Peptostreptococcus sp., *Neisseria gonorrhoeae, Escherichia coli*, Citrobacter sp., Shigella sp., *Klebsiella pneumoniae*, Enterobacter sp., Serratia sp., Proteus sp., *Pseudomonas aeruginosa, Haemophilus influenzae*, Acinetobacter sp., Campylobacter sp., and *Chlamydozoon trachomatis*.

Diseases which are caused by these pathogenic microorganisms and can be prevented, alleviated or cured by the compounds of the present invention include folliculitis, furuncle, furunclosis, carbuncle, erysipelas, phlegmon, lymphangitis/lymphadenitis, felon, subcutaneous abscess, spiradenitis, acne conglobata, infectious atheroma, perianal abscess, mastadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epidigymitis, gonococcal urethritis, nongonococcal urethritis, cholecystitis, cholangitis, bacillary dysentery, enteritis, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, septicemia, meningitis, and skin infections.

The compounds of the present invention are also effective on various microorganisms causing veterinary diseases, such as those belonging to the genera Escherichia sp., Salmonella sp., Pasteurella sp., Haemophilus sp., Bordetella sp., Staphylococcus sp., and Mycoplasma sp..

Illustrative examples of such veterinary diseases include those of fowl, such as colibacillosis, pullorum disease, avian paratyphosis, fowl cholera, infectious coryza, staphylomycosis, and mycoplasmosis; those of pigs, such as colibacillosis, salmonellosis, pasteurellosis, haemophylus infections, atrophic rhinitis, exudative epidermitis, and mycoplasmosis; those of cattle, such as colibacillosis, salmonellosis, hemorrhagic septicemia, mycoplasmosis, bovine contagious pleuropneumonia, and bovine mastitis; those of dogs, such as colisepsis, salmonellosis, hemorrhagic septicemia, pyometra, and cystitis; those of cats, such as hemorrhagic pleurisy, cystitis, chronic rhinitis, and haemophylus infections; and those of kittens, such as bacterial entritic and mycoplasmosis.

Dosage forms of the pharmaceutical preparations containing one or more compounds of the present invention as an active ingredient can be appropriately selected according to the administration route and can be prepared by conventional preparation methods. Examples of dosage forms for oral administration include tablets, powders, granules, capsules, solutions, syrups, elixirs, and oily or aqueous suspensions.

Injectable preparations may contain excipients, such as stabilizers, preservatives, and solubilizers. The injectable solution which may contain these excipients may be put into a container, e.g., ampoules and vial vessels, and solidified by, for example, lyophilization to prepare a solid preparation which is dissolved on use. The container may contain either a single dose or multiple doses.

Topical preparations include solutions, suspensions, emulsions, ointments, gels, creams, lotions, and sprays.

Solid preparations may contain pharmaceutically acceptable additives, such as fillers, extenders, binders, humectants, absorption accelerators, wetting agents, adsorbents, and lubricants.

Liquid preparations include solutions, suspensions, and emulsions. They may contain excipients, such as suspending agents, emulsifiers, stabilizers, and preservatives.

The compound of the present invention may also be administered to animals as oral or non-oral veterinary medicines. And such medicines may be administered in the form of a mixture with feedstuff or water. The preparations for veterinary medicine or additives can be prepared according to the customary method of the field and such preparations include powders, fine granules, granules, solubilized powders, syrups, solutions and injections.

The following are the examples of the formulations and these are purely illustrative and in no way to be interpreted as restrictive.

| FORMULATION EXAMPLE 1 | |
|---|---|
| Capsules | |
| Compound of Example 1 | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| Total: | 150.0 mg (per capsule) |

| FORMULATION EXAMPLE 2 | |
|---|---|
| Solution | |
| Compound of Example 1 | 1 to 10 g |
| Acetic acid or sodium hydroxide | 0.5 to 2 g |
| Ethyl p-hydroxybenzoate | 0.1 g |
| Purified water | 88.9 to 98.4 g |
| Total: | 100 g |

| FORMULATION EXAMPLE 3 | |
|---|---|
| Powder for Admixing with Feedstuff | |
| Compound of Example 1 | 1 to 10 g |
| Corn starch | 98.5 to 89.5 g |
| Light anhydrous silicic acid | 0.5 g |
| Total: | 100 g |

Although the disclosure illustrates and describes a preferred embodiment of this invention, it is to be understood that it is not restricted thereto.

The following examples are further illustrative of the present invention but should by no means be construed as limiting its scope.

The antibacterial activity assays were preformed by the method specified by Japan Society of Chemotherapy (Chemotherapy 29(1), 76 (1981)). The table of antibacterial activity is followed by the reaction schemes for the synthesis of various spiro ring-containing cyclic amine derivatives, intermediate compounds for synthesis of quinolone rings and synthesis of various spiro compounds.

REFERENCE EXAMPLE 1

N-[1,(R)-phenylethyl]-3-oxobutanamide

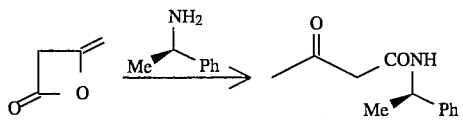

A solution of 21 g of diketene in 15 ml of dried methylene chloride was added dropwise to a solution of 31 g of (R)-D-(+)-phenylethylamine in 85 ml of dried methylene chloride with stirring while cooling with ice. The maximum temperature of the reaction mixture reached during the dropwise addition was 15° C. The resulting solution was stirred at room temperature for 15 hours. The reaction mixture was washed successively with a 10% citric acid aqueous solution and a saturated sodium hydrogencarbonate aqueous solution and dried over anhydrous sodium sulfate. The solvent was removed under reduced pressure to yield 53.7 g of the titled compound.

$^1$H-NMR (CDCl$_3$) δ:1.48 (3 H, d, J=5.4 Hz), 2.24 (3 H, s), 3.40 (2 H, s), 5.14 (1 H, q, J=5.4 Hz), 7.35 (5H, s)

REFERENCE EXAMPLE 2

2,2-Dimethyl-N-[1-(R)-phenylethyl]-3-oxobutanamide

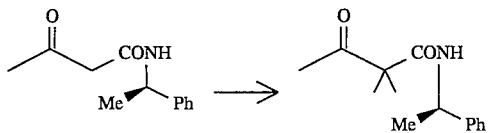

To a solution of 48.5 g of N-[1-(R)-phenylethyl]-3-oxobutanamide in 250 ml of dried N,N-dimethylformamide was added 84 g of methyl iodide, and 65.3 g of potassium carbonate was added thereto under cooling with ice, followed by stirring at room temperature for 1 week. After 72 hours from the start of the reaction, 10 g of methyl iodide and 35 g of potassium carbonate were added. After 144 hours from the start of the reaction, 10 g of methyl iodide was further added. Any insoluble matter was removed from the reaction mixture by filtration, and the solvent of the filtrate was removed under reduced pressure. To the residue was added 100 ml of water, and the mixture was extracted with 400 ml of ethyl acetate. The extract was washed with water and dried over anhydrous sodium sulfate. The solvent was removed under reduced pressure to yield 50 g of a crude crystal of the titled compound. The crude crystal was washed with isopropyl alcohol to yield 33 g of a purified product.

$^1$H-NMR (CDCl$_3$) δ: 1.40 (3H, s), 1.42 (3H, s), 1.50 (3H, d, J=5.4 Hz), 2.17 (3H, s), 5.08 (1H, q, J=5.4 Hz), 6.18 (1H, brs), 7.32 (5H, s)

REFERENCE EXAMPLE 3

2-Methyl-2-[1-methyl-1-[N-(R)-1-phenylethyl]carbamoyl]ethyl-1,3-dioxolane

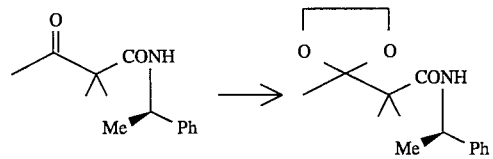

In 220 ml of benzene was dissolved 11.65 g of 2,2-dimethyl-N-[1-(R)-phenylethyl]-3-oxobutanamide, and to the solution were added 18 g of ethylene glycol and 1 g of p-toluenesulfonic acid. The mixture was heated under reflux for 3 days while removing produced water by a Dean-Stark apparatus. After cooling, the reaction mixture was poured into 50 ml of a saturated sodium hydrogencarbonate aqueous solution, followed by shaking. The organic layer was separated and dried over anhydrous sodium sulfate. The solvent was removed under reduced pressure to yield 15.2 g of the titled compound.

$^1$H-NMR (CDCl$_3$) δ: 1.20 (3H, s), 1.22 (3H, s), 1.23 (3H, s), 1.50 (3H, d, J=5.4 Hz), 3.95 (4H, s), 5.12 (1H, q, J=5.4 Hz), 7.12 (1H, brs.), 7.32 (5H s)

REFERENCE EXAMPLE 4

2-Bromomethyl-2-[1-methyl-1-[N-(R)-1-phenylethyl]carbamoyl]ethyl-1,3-dioxolane

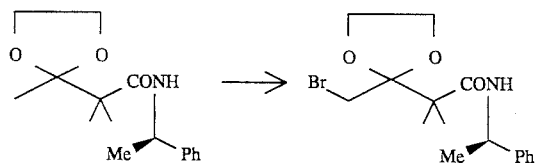

In 400 ml of dried 1,4-dioxolane was dissolved 37.68 g of 2-methyl-2-[1-methyl-1-[N-(R)-1-phenylethyl] carbamoyl]ethyl-1,3-dioxolane, and 22 g of bromine was added thereto dropwise at room temperature, followed by stirring for 4 hours. The solvent was removed from the reaction mixture under reduced pressure, and to the residue was added 500 ml of chloroform. The chloroform layer was washed successively with a saturated sodium hydrogencarbonate aqueous solution, a 5% sodium thiosulfate aqueous solution, and water, and dried over anhydrous sodium sulfate. The solvent was removed under reduced pressure to yield 45.25 g of the titled compound.

$^1$H-NMR (CDCl$_3$) δ:1.24 (3H, d, J=3.6 Hz), 1.42 (3H, s), 1.54 (3H, s), 3.58 (2H, ABq, J=10.8 Hz), 3.90–4.50 (4H, m), 5.05 (1H, q, J=3.6 Hz), 7.00 (1H, brs), 7.30 (5H, s)

REFERENCE EXAMPLE 5

9,9-Dimethyl-8-oxo-7-[1-(R)-phenylethyl]-7-aza-,1,4-dioxaspiro[4,4]nonane

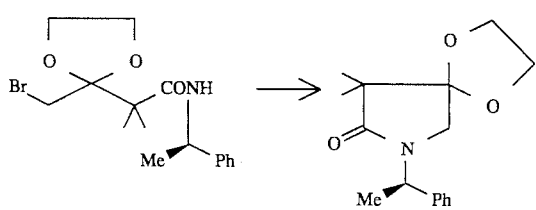

In 150 ml of dried N,N-dimethylformamide was dissolved 45.25 g of 2-bromomethyl-2-[1-methyl-1-[N-(R)-1-phenylethyl] carbamoyl]ethyl-1,3-dioxolane, and 6.5 g of 60% sodium hydride was added thereto under ice-cooling, followed by stirring at room temperature for 18 hours. The reaction mixture was poured into 300 ml of ice-water and extracted with 600 ml of benzene. The extract was washed with water and dried over anhydrous sodium sulfate. The solvent was removed under reduced pressure, and the residue was purified by column chromatography (packed with 350 g of silica gel) using a 3:1 (by volume) mixture of n-hexane and ethyl acetate as an eluent. The fractions containing the desired compound were combined, and the solvent was removed therefrom under reduced pressure to yield 18.23 g of the titled compound as an eluent.

$^1$H-NMR (CDCl$_3$) δ:1.18 (3H, d, J=4.0 Hz), 1.50 and 1.58 (each 3H, s), 3.04 (2H, ABq, J=10 Hz), 3.75–4.10 (4H, m), 5.60 (1H, q, J=4 Hz), 7.32 (5H, s)

REFERENCE EXAMPLE 6

3,3-Dimethyl-1-[1,(R)-phenylethyl]-pyrrolidine-2,4-dione

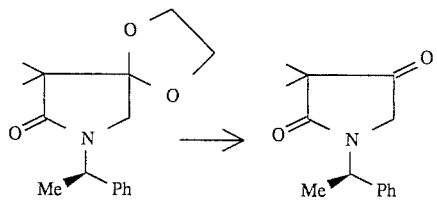

In 250 ml of acetone was dissolved 18.23 g of 9,9-dimethyl-8-oxo-7-[1-(R)-phenylethyl]-7-aza-1,4-dioxaspiro -[4,4]nonane, and 70 ml of hydrochloric acid and 20 g of p-toluenesulfonic acid were added to the solution. The mixture was heated under reflux for 20 hours. After 7 hours from the start of the reaction, 20 g of p-toluenesulfonic acid was added to the reaction mixture. After the reaction, acetone was removed from the mixture under reduced pressure, and the residue was extracted with 400 ml of chloroform. The chloroform layer was washed with a saturated sodium hydrogencarbonate aqueous solution and dried over anhydrous sodium sulfate. The solvent was removed under reduced pressure, and the residue was purified by silica gel (350 g) column chromatography using a 4:1 (by volume) mixture of n-hexane and ethyl acetate as an eluent. From combined fractions containing the desired compound, the solvent was removed under reduced pressure to yield 11.85 g of the titled compound.

$^1$H-NMR (CDCl$_3$) δ:1.20 and 1.26 (each 3H, s), 1.60 (3H, d, J=7.2 Hz), 3.60 (2H, ABq, J=16 Hz), 5.80 (1H, q, J=7.2 Hz), 7.32 (5H, s)

REFERENCE EXAMPLE 7

3,3-Dimethyl-4-hydroxyimino-1-[1-(R)-phenylethyl]-pyrrolidin-2-one

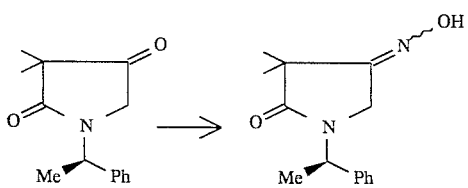

In 100 ml of ethanol was dissolved 11.85 g of 3,3-dimethyl-1-[1-(R)-phenylethyl]-pyrrolidine-2,4-dione. To the solution were added 8 g of hydroxylamine hydrochloride and 45 ml of triethylamine, followed by refluxing for 1 hour. The solvent was removed under reduced pressure, and to the residue was added 300 ml of chloroform. The chloroform solution was washed successively with a 10% citric acid aqueous solution and water and dried over anhydrous sodium sulfate. The solvent was removed under reduced pressure to yield 11.5 g of the titled compound.

$^1$H-NMR (CDCl$_3$) δ:1.30 and 1.34 ( each 3H, s ), 1.58 ( 3H, d, J=7.2 Hz), 3.90 (2H, ABq, J=16.2 Hz), 5.65 (1H, q, J=7.2 Hz), 7.36 (5H, s)

REFERENCE EXAMPLE 8

4-Amino-3,3-dimethyl-1-[1-(R)-phenylethyl]-Pyrrolidin-2-one

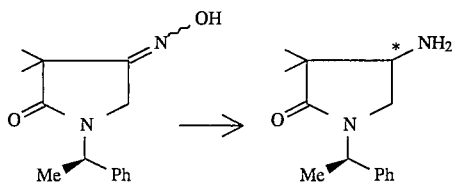

In 300 ml of methanol was dissolved 11.5 g of 3,3-dimethyl-4-hydroxyimino-1-[1-(R)-phenylethyl]-Pyrrolidin-2-one, and about 20 ml of Raney nickel washed with methanol was added to the solution. Reduction was conducted at room temperature for 16 hours in an egg-plant type flask. The catalyst was removed by filtration, and the solvent of filtrate was removed under reduced pressure. The residue was subjected to silica gel (400 g) column chromatography using a 30:1 (by volume) mixture of chloroform and methanol as an eluent to yield 3.75 g of Fraction 1 (lower polar material) and 10.2 g of a mixture of Fraction 1 and Fraction 2 (higher polar material).

$^1$H-NMR (CDCl$_3$) δ (lower polar compound): 0.95 and 1.18 (each 3H, s), 1.52 (3H, d, J=7.2 Hz), 2.40–2.55 (1H, m), 3.00–3.50 (2H, m), 5.52 (1H, q, J=7.2 Hz), 7.30 (5H, s)

REFERENCE EXAMPLE 9

4-Amino-3,3-dimethyl-1-[1-(R)-phenylethyl]-pyrrolidine

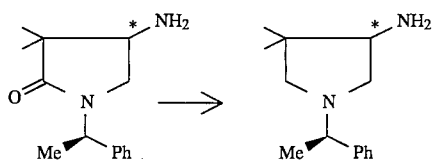

In 150 ml of dried tetrahydrofuran was dissolved 3.7 g of Fraction 1 obtained in Reference Example 8 (low polar 4-amino-3,3-dimethyl-1-[1-(R)-phenylethyl]-pyrrolidin-2-one), and 2 g of lithium aluminum hydride was slowly added thereto while cooling with ice, followed by heating under reflux for 13 hours. After cooling, 2 ml of water, 2 ml of a 15% sodium hydroxide aqueous solution, and 6 ml of water were added to the reaction mixture in this order while ice-cooling, followed by stirring at room temperature for 1 hour. Any insoluble matter was removed by filtration, and the solvent was removed from the filtrate under reduced pressure to yield 3.69 g of the titled compound. The compound thus recovered was used in the next reaction without any further purification.

REFERENCE EXAMPLE 10

4-t-Butoxycarbonylamino-3,3-dimethyl-1-[1-(R)-phenylethyl]-pyrrolidine

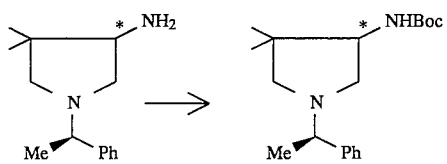

In 40 ml of dried tetrahydrofuran was dissolved 3.69 g of 4-amino-3,3-dimethyl-1-[1-(R)-phenylethyl]-pyrrolidine obtained in Reference Example 9, and 4.92 g of 2-(t-butoxycarbonylamino)-2-phenylacetonitrile (BOC-ON) was added thereto under ice-cooling. The mixture was stirred at room temperature for 1 hour. The solvent was removed under reduced pressure, and to the residue was added 100 ml of ethyl acetate. The mixture was washed three times with a 1N sodium hydroxide aqueous solution. The ethyl acetate layer was dried over anhydrous sodium sulfate, and the solvent was removed under reduced pressure. The residue was purified by silica gel (200 g) column chromatography using a 1% and 5% methanol-containing chloroform as an eluent to yield 4.32 g of the titled compound.

$^1$H-NMR (CDCl$_3$) δ: 1.00 and 1.16 (3H, s), 1.40 (3H, d, J=7.2 Hz), 1.52 (9H, s), 2.00–3.62 (5H, m), 3.85–4.10 (1H, m), 4.90 (1H, brs), 7.38 (5H, s)

REFERENCE EXAMPLE 11

4-t-Butoxycarbonylamino-3,3-dimethyl-pyrrolidine

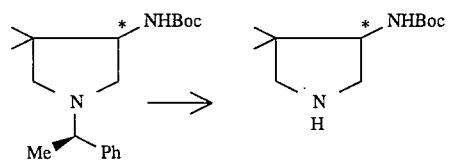

In 90 ml of ethanol was dissolved 4.32 g of 4-t-butoxycarbonylamino-3,3-dimethyl-1-[1-(R)-phenylethyl]-pyrrolidine, and 4 g of 10% palladium-on-carbon was added thereto to conduct reduction at a hydrogen pressure of 4 atm. while heating by irradiating with a tungsten lamp. After about 7 hours, the catalyst was removed by filtration, and the solvent of filtrate was removed under reduced pressure. To the residue was added 200 ml of ethyl acetate, followed by washing twice with a 10% citric acid aqueous solution. The citric acid aqueous solution layer was made alkaline (pH: ca. 10) with a sodium hydroxide aqueous solution and then extracted with 200 ml of chloroform. The extract was dried over anhydrous sodium sulfate, and the solvent was removed under reduced pressure to yield 2.5 g of the titled compound.

$^1$H-NMR (CDCl$_3$) δ: 0.98 and 1.08 (each 3H, s), 1.48 (9H, s), 2.30–4.00 (6H, m), 4.50 (1H, brs)

EXAMPLE 10-(4-Amino-3,3-dimethyl-1-pyrrolidinyl)-9-fluoro-2,3-dihydro-3-(S)-3-methyl-7-oxo-7H-pyrido[1,2,3-de][1,4]-benzoxazine-6-carboxylic Acid

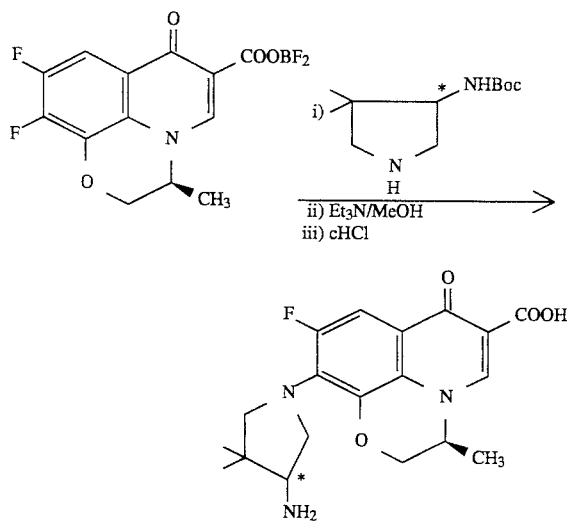

In 3 ml of dried dimethyl sulfoxide was suspended 493.5 mg of 9,10-difluoro-2,3-dihydro-3-(S)-3-methyl-7-oxo-7H-pyrido[1,2,3-de][1,4]benzoxazine-6-carboxylic acid difluoroboron chelate. To the suspension were added 800 mg of 4-t-butoxycarbonylamino-3,3-dimethyl-pyrrolidine obtained in Reference Example 11 and 0.5 ml of triethylamine at room temperature, followed by stirring for 30 minutes. Water was added to the reaction mixture while ice-cooling, and the precipitated crystal was collected by filtration and washed with water. The crystal was dissolved in 30 ml of 90% methanol, and 4 ml of triethylamine was added thereto, followed by refluxing for about 6 hours. The solvent was removed from the reaction mixture under reduced pressure. To the residue was added 5 ml of concentrated hydrochloric acid, followed by stirring at room temperature for about 1 hour. The reaction mixture was washed with chloroform, and the aqueous layer was adjusted to pH 7 with 50% and 1N sodium hydroxide aqueous solutions and then extracted with 100 ml of chloroform. The chloroform layer was dried over anhydrous sodium sulfate, and the solvent was removed under reduced pressure to yield about 500 mg of a crude crystal of the titled compound. The crude product was recrystallized from ethanol containing a small amount of aqueous ammonia while simultaneously conducting a treatment with activated carbon to thereby yield 337 mg of a crystal.

Melting point: 263°–268° C. (dec.)

$[\alpha]_D$: +147.6° (c=1.085, 1N NaOH)

Elementary Analysis for $C_{19}H_{22}N_3O_4F$:

Calcd. (%): C 60.79; H 5.91; N 11.19

Found (%): C 60.59; H 5.84; N 10.99

TEST EXAMPLE

Antimicrobial activity of the compound of Example 1 and, for comparison, 10-(3-amino-1-pyrrolidinyl)-9-fluoro-2,3-dihydro-3-(S)-3-methyl-7-oxo-7H-pyrido[1,2,3-de][1,4]-benzoxazine-6-carboxylic acid on various test organisms listed below was determined in accordance with the method specified by Japan Society of Chemotherapy (Chemotherapy 29(1), 76 (1981)), and the minimum inhibitory concentrations (μg/ml) obtained are shown in Table 1 below.

TABLE 1

| Test Organism | Compound of Example 1 | Comparative Compound |
|---|---|---|
| *S. aureaus*, 209P | <0.1 | <0.1 |
| *S. aureaus*, Smith | <0.1 | <0.1 |
| *S. epidermidis*, 56500 | 0.1 | 0.20 |
| *S. epidermidis*, 56556 | <0.1 | 0.20 |
| *Str. pyogenes*, G-36 | 0.39 | 0.78 |
| *Str. mitis*, IID 685 | 0.10 | 0.78 |
| *Str. fecalis*, ATCC 19433 | 0.20 | 0.78 |

While the invention has been described in detail and with reference to specific examples thereof, it will be apparent to one skilled in the art that various changes and modifications can be made therein without departing from the spirit and scope thereof.

What is claimed is:

1. An optically active pyridobenzoxazine derivative or salt thereof, wherein said derivative is 10-(4-Amino-3,3-dimethyl-1-pyrrolidinyl)-9-fluoro-2,3-dihydro-3-(S)-3-methyl-7-oxo-7H-pyrido[1,2,3-de][1,4]benzoxazine-6-carboxylic acid.

* * * * *